US011001811B2

(12) United States Patent
Murphy et al.

(10) Patent No.: US 11,001,811 B2
(45) Date of Patent: May 11, 2021

(54) MULTI-LAYER AIRWAY ORGANOIDS AND METHODS OF MAKING AND USING THE SAME

(71) Applicant: Wake Forest University Health Sciences, Winston-Salem, NC (US)

(72) Inventors: Sean V. Murphy, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 372 days.

(21) Appl. No.: 15/768,100

(22) PCT Filed: Oct. 14, 2016

(86) PCT No.: PCT/US2016/056947
§ 371 (c)(1),
(2) Date: Apr. 13, 2018

(87) PCT Pub. No.: WO2017/066507
PCT Pub. Date: Apr. 20, 2017

(65) Prior Publication Data
US 2018/0291350 A1 Oct. 11, 2018

Related U.S. Application Data

(60) Provisional application No. 62/404,931, filed on Oct. 6, 2016, provisional application No. 62/242,611, filed on Oct. 16, 2015.

(51) Int. Cl.
| | |
|---|---|
| *C12N 5/071* | (2010.01) |
| *C12M 3/00* | (2006.01) |
| *C12M 3/06* | (2006.01) |
| *C12M 1/00* | (2006.01) |

(52) U.S. Cl.
CPC .......... *C12N 5/0697* (2013.01); *C12M 21/08* (2013.01); *C12M 23/16* (2013.01); *C12M 23/22* (2013.01); *C12N 5/0688* (2013.01); *C12N 2502/27* (2013.01); *C12N 2502/28* (2013.01); *C12N 2533/54* (2013.01); *C12N 2533/90* (2013.01)

(58) Field of Classification Search
CPC ................ C12N 5/0697; C12N 5/0688; C12N 2502/27; C12N 2502/28; C12N 2533/54; C12N 2533/90; C12M 21/08; C12M 23/16; C12M 23/22
See application file for complete search history.

(56) References Cited

U.S. PATENT DOCUMENTS

| | | | |
|---|---|---|---|
| 5,750,329 A | 5/1998 | Quinn et al. | |
| 8,338,114 B1 | 12/2012 | Goodwin | |
| 8,647,837 B2 | 2/2014 | Mahmood et al. | |
| 2009/0227025 A1 | 9/2009 | Nichols et al. | |
| 2012/0045770 A1* | 2/2012 | Pongracz | C12N 5/0688 435/6.12 |
| 2013/0190210 A1 | 7/2013 | Murphy et al. | |
| 2014/0038279 A1 | 2/2014 | Ingber et al. | |
| 2014/0147482 A1 | 5/2014 | Mahmood et al. | |
| 2014/0335496 A1 | 11/2014 | Grego et al. | |

FOREIGN PATENT DOCUMENTS

| | | |
|---|---|---|
| JP | 2006174837 A | 7/2006 |
| WO | 2015138034 A2 | 9/2015 |

OTHER PUBLICATIONS

Sellgren et al., A biomimetic multicellular model of the airways using primary human cells. Lab on a Chip, vol. 14 (2014) pp. 3349-3358. (Year: 2014).*
Choe et al., An in vitro airway wall model of remodeling. American Journal of Physiology: Lung cellular and molecular physiology, vol. 285, No. 2 (Aug. 2003) p. L427-L433. (Year: 2003).*
Skolimowski et al., "Microfluidic model of cystic fibrosis bronchi" 15th International Conference on Miniaturized Systems for Chemistry and Life Sciences (Oct. 2011) 3 pages. (Year: 2011).*
Extended European Search Report corresponding to European Patent Application No. 16856231.2 (8 Pages) (dated Feb. 25, 2019).
Nichols et al. "Novel in vitro respiratory models to study lung development, physiology, pathology and toxicology" Stem Cell Research & Therapy 4(Suppl 1):S7 (5 Pages) (Dec. 2013).
Sellgren et al. "A biomimetic multicellular model of the airways using primary human cells" Lab on a Chip 14(17):3349-3358 (Jan. 2014).
Skolimowski et al. "Microfluidic Model of Cystic Fibrosis Bronchi" 15th International Conference on Miniaturized Systems for Chemistry and Life Sciences (3 pages) (Oct. 2011).
Bhatia and Ingber, "Microfluidic organs-on-chips," Nature Biotechnology 32:760-772 (2014)(Abstract Only).
Booth et al. "Acellular Normal and Fibrotic Human Lung Matrices as a Culture System for In Vitro Investigation" American Journal of Respiratory and Critical Care Medicine 186(9):866-876 (2012).
Guilbault et al. "Cystic Fibrosis Mouse Models" American Journal of Respiratory Cell and Molecular Biology 36(1):1-7 (2007).
Lang et al. "Three-dimensional culture of hepatocytes on porcine liver tissue-derived extracellular matrix" Biomaterials (2011)(Abstract Only) 32(29):7042-7052.
Mirmalek-Sani et al. "Porcine pancreas extracellular matrix as a platform for endocrine pancreas bioengineering" Biomaterials 34(22):5488-5495 (2013).
Orlando et al. "Production and Implantation of Renal Extracellular Matrix Scaffolds From Porcine Kidneys as a Platform for Renal Bioengineering Investigations" Annals of Surgery 256(2):363-370 (2012).

(Continued)

*Primary Examiner* — Kara D Johnson
(74) *Attorney, Agent, or Firm* — Myers Bigel P.A.

(57) ABSTRACT

Provided herein are artificial lung organoids. The artificial lung organoids may include an epithelial cell layer comprising mammalian lung epithelial cells, a stromal cell layer comprising mammalian lung fibroblast cells and an endothelial cell layer comprising mammalian endothelial cells. The artificial lung organoids may optionally include a porous membrane between said epithelial cell layer and said stromal cell layer and/or between said stromal cell layer and said endothelial lung cell layer.

31 Claims, 4 Drawing Sheets

(56) References Cited

OTHER PUBLICATIONS

International Search Report and Written Opinion of the International Search Authority corresponding to International Patent Application No. PCT/US2016/056947 dated Jan. 13, 2017 (10 pages).
Mondrinos et al. "Engineering De Novo Assembly of Fetal Pulmonary Organoids" Tissue Engineering Part A 20 (21-22):2892-28907 (Jun. 24, 2014) Abstract Only.
Shamir et al. "Three-dimensional organotypic culture: experimental models of mammalian biology and disease" Nature Reviews Molecular Cell Biology 15:647-664 (Sep. 17, 2014) Abstract Only.
Wong et al. "Generation of Lung Epithelium from Pluripotent Stem Cells" Current Pathobiology Reports 1:137-145 (Apr. 3, 2013).
Perros et al. "TLR4 signalling and pulmonary stromal cells is critical for inflammation and immunity in the airways" Respiratory Research 12(125):1-8 (Dec. 1, 2011).
Japanese Office Action corresponding to JP 2018-519447; dated Sep. 1, 2020 (9 pages, including English translation).
Skardal, Aleksander, et al., "A hydrogel bioink toolkit for mimicking native tissue biochemical and mechanical properties in bioprinted tissue constructs", Acta Biomaterialia, 25, 2015, 24-34.

\* cited by examiner

US 11,001,811 B2

MULTI-LAYER AIRWAY ORGANOIDS AND METHODS OF MAKING AND USING THE SAME

CROSS REFERENCE TO RELATED APPLICATIONS

This application is a 35 U.S.C. § 371 national stage application of PCT International Application No. PCT/US2016/056947, filed on Oct. 14, 2016, which claims priority from U.S. Provisional Patent Application Nos. 62/242,611, filed Oct. 16, 2015, and 62/404,931, filed Oct. 6, 2016, the contents of which are incorporated herein by references in their entireties. The above-referenced PCT International Application was published in the English Language as International Publication No. WO 2017/066507 A1 on Apr. 20, 2017.

FIELD OF THE INVENTION

This invention relates generally to multi-layer airway organoids and methods of making and using of the same.

BACKGROUND OF THE INVENTION

The study of respiratory infection is significantly limited by a lack of suitable in vivo and in vitro models to investigate interactions between the respiratory epithelium, infection and disease. For example, animal models often do not acquire the pathological abnormalities in the airways and lungs seen in humans. See, e.g., Guilbault et al., *Cystic fibrosis mouse models*, American Journal of Respiratory Cell and Molecular Biology. 2007; 36(1):1-7. Additionally, most in vitro models are unable to create the differentiated tissue components and structural complexity of the airway epithelium. See, e.g., Lang et al., *Three-dimensional culture of hepatocytes on porcine liver tissue-derived extracellular matrix*, Biomaterials. 2011; 32(29):7042-7052.

Primary airway epithelial cells, derived from cadaver tissue and expanded ex vivo on 2D plastic culture surfaces, remain the current standard for disease modeling and therapy evaluation in vitro. However, these techniques present cells with artificial conditions, including two-dimensional (2D) growth surfaces that are several magnitudes stiffer than most soft tissues, and lack of important signals from the tissue microenvironment. As a consequence, they impose a selective pressure on the cells that substantially alter their heterogeneity and functional properties. See, e.g., Anderson et al., *Tumor morphology and phenotypic evolution driven by selective pressure from the microenvironment*, Cell 127.5 (2006): 905-915. For example, plastic culture expanded cells often become non-ciliated, a significant limitation in studying bacterial pathogens of the airways, which often display preferential attachment to ciliated respiratory epithelium in vivo. See, e.g., Matsui et al., *Evidence for periciliary liquid layer depletion, not abnormal ion composition, in the pathogenesis of cystic fibrosis airways disease*. Cell. 1998; 95(7):1005-1015; Gray et al., *Mucociliary differentiation of serially passaged normal human tracheobronchial epithelial cells*. American Journal of Respiratory Cell and Molecular Biology. 1996; 14(1):104-112. The lack of physiological airway models represents a significant limitation to the study of the pathogenesis of infection in the airway.

US Patent Application Publication 2009/0227025 to Nichols et al. discussed the use of progenitor or stem cells to generate new lung tissue in an in vitro system using microgravity conditions. U.S. Pat. No. 8,647,837 to Mahmood et al. and U.S. Pat. No. 5,750,329 to Quinn et al. discuss the use of alveolar and endothelial cell layers in an artificial tissue construct for the study of lung diseases concerning the alveoli, or air sacs, of the lungs. U.S. Pat. No. 8,338,114 to Goodwin discusses three-dimensional (3D) human broncho-epithelial tissue-like assemblies produced in a rotating wall vessel with microcarriers by co-culturing mesenchymal bronchial-tracheal cells and bronchial epithelium cells. However, there remains a need for improved in vitro systems that can be used for study of infection and pathogenesis affecting the lungs.

SUMMARY OF THE INVENTION

Provided herein is an artificial mammalian lung organoid, comprising:
(a) an epithelial cell layer comprising mammalian lung epithelial cells;
(b) a stromal cell layer comprising mammalian lung fibroblast cells; and
(c) an endothelial cell layer comprising mammalian endothelial cells (e.g., microvascular endothelial cells).

In some embodiments, the organoid further comprises a porous membrane (e.g., a polymeric material) between said epithelial cell layer and said stromal lung cell layer and/or between said stromal lung cell layer and said endothelial lung cell layer.

In some embodiments, the cells of the lung epithelial cell layer are polarized. In some embodiments, the cells of the lung endothelial cell layer, stromal cell layer and/or epithelial cell layer are human.

In some embodiments, the lung organoid is an upper airway lung organoid. In some embodiments, the mammalian lung epithelial cells are bronchial epithelial cells. In some embodiments, the mammalian lung epithelial cells comprise normal bronchial epithelial cells. In some embodiments, the mammalian lung epithelial cells comprise diseased bronchial epithelial cells.

In some embodiments, the bronchial epithelial cells comprise basal, goblet, ciliated and/or clara cells.

In some embodiments, the ratio of mammalian lung fibroblast cells of the stromal layer and mammalian endothelial cells of the endothelial cell layer is from 2:1 to 1:2. In some embodiments, the ratio of mammalian lung fibroblast cells of the stromal layer and mammalian epithelial cells of the epithelial cell layer is from 2:1 to 1:2. In some embodiments, the ratio of mammalian endothelial cells of the endothelial layer and mammalian epithelial cells of the epithelial cell layer is from 2:1 to 1:2.

In some embodiments, the porous membrane is coated on one or both sides with laminin, collagen type I, collagen type IV, fibronectin, elastin, a lung tissue-derived extracellular matrix composition, or a combination thereof.

In some embodiments, the lung organoid is infected with a lung pathogen. In some embodiments, the lung organoid is infected with *Bordetella pertussis* or *Pseudomonas aeruginosa*.

Also provided is a microfluidic device comprising the lung organoid as taught herein. The microfluidic device may include a housing comprising a chamber and a channel. The lung organoid may be in the chamber, the channel may be configured to provide fluid connection of the lung organoid to a fluid inlet and a fluid outlet, and said fluid inlet and said fluid outlet may be connected to a fluid reservoir.

In some embodiments, at least a portion of the housing may be transparent. In some embodiments, the endothelial cell layer of the lung organoid is in fluid connection with a liquid (e.g., media) in the device. In some embodiments, the epithelial cell layer of the lung organoid is in fluid connection with a gas (e.g., air). In some embodiments, the epithelial cell layer of the lung organoid is in fluid connection with a liquid (e.g., media).

Methods of making the lung organoid as taught herein are also provided. According to some embodiments, the method may include:

depositing the endothelial cell layer comprising the mammalian endothelial cells onto a first side of the porous membrane;

depositing the stromal cell layer comprising the mammalian lung fibroblast cells onto a second side of the porous membrane that is opposite the first side of the porous membrane; and depositing the epithelial cell layer comprising the mammalian lung epithelial cells directly onto the stromal cell layer.

In some embodiments, the method may include:

providing a hydrogel including the mammalian lung fibroblast cells;

depositing the endothelial cell layer comprising the mammalian endothelial cells onto a first side of the hydrogel; and depositing the epithelial cell layer comprising the mammalian lung epithelial cells onto an a second side of the hydrogel that is opposite the first side of the hydrogel.

In some embodiments, the hydrogel may be cross-linked. In some embodiments, the hydrogel may include gelatin, fibrinogen, gellan gum, pluronics (poloxamers), alginate, chitosan, hyaluronic acid, cellulose and/or collagen.

BRIEF DESCRIPTION OF THE DRAWINGS

FIG. 4 (b) is a schematic diagram of a microfluidic support system according to some embodiments of the present invention; and FIG. 4 (c) is an image of a microfluidic support system according to some embodiments of the present invention.

DETAILED DESCRIPTION OF ILLUSTRATIVE EMBODIMENTS

Figure 1:
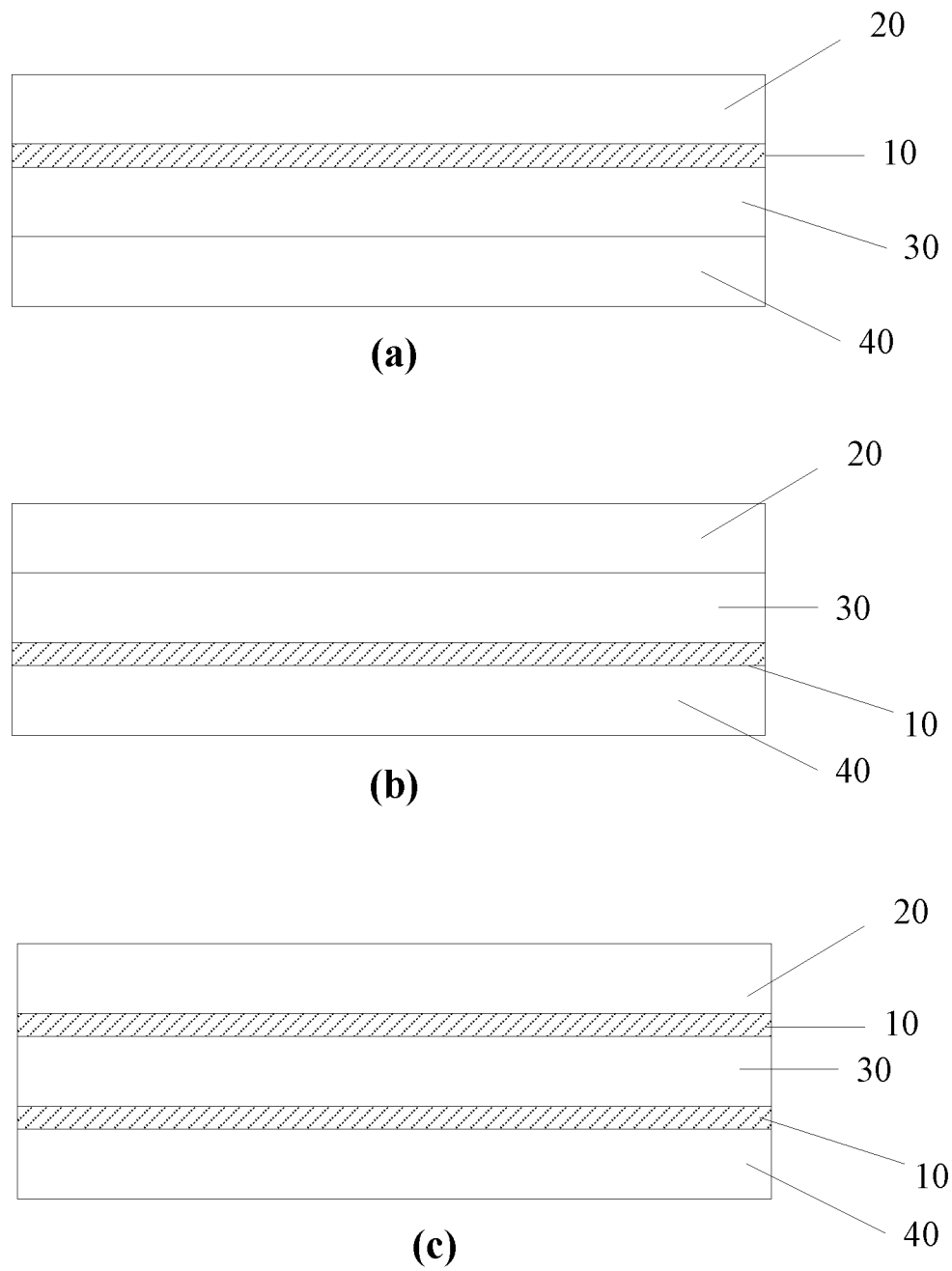
FIGS. 1 (a), (b) and (c) provide schematic illustrations of the layers of lung organoids including membrane(s) according to some embodiments of the present invention.

The present invention is now described more fully hereinafter. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, steps, operations, elements components and/or groups or combinations thereof, but do not preclude the presence or addition of one or more other features, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

"Cells" as used herein are, in general, mammalian cells, such as dog, cat, cow, goat, horse, sheep, mouse, rabbit, rat, etc. cells. In some preferred embodiments the cells are human cells. Suitable cells are known and are commercially available, and/or may be produced in accordance with known techniques. In some embodiments, the cells are harvested from a donor and passaged. In some embodiments, the cells are differentiated from cell lines. In some embodiments, the cells are derived from adult stem cells (bone marrow, peripheral blood, umbilical cord blood, wharton's jelly in the umbilical cord or from placental tissues), embryonic stem cells, amniotic fluid stem cells, or any other source of stem cells that can be differentiated into the tissue of interest.

"Mammalian" as used herein refers to both human subjects (and cells sources) and non-human subjects (and cell sources or types), such as dog, cat, mouse, monkey, etc. (e.g., for veterinary purposes).

"Extracellular Matrix" (ECM) as used herein refers to extracellular molecules secreted by cells that provides structural and biochemical support to the surrounding cells. The ECM is normally composed of an interlocking mesh of fibrous proteins and polysaccharides such as glycosaminoglycans (GAGs). "Extracellular Matrix composition" as used herein refers to a composition including ECM proteins.

"Extracellular Matrix Proteins" (or "ECM proteins") as used herein are known, and include but are not limited to those described in Y. Zhang et al., US Patent Application Publication No. 2013/0288375. Examples of ECM proteins include, but are not limited to, laminin, collagen type I, collagen type IV, fibronectin and elastin.

"Organoid" as used herein refers to an artificial, in vitro construct created to mimic or resemble the functionality and/or histological structure of an organ or portion thereof.

"Media" or "culture media" as used herein refers to an aqueous based solution that is provided for the growth, viability, or storage of cells used in carrying out the present invention. A media or culture media may be natural or artificial. A media or culture media may include a base media and may be supplemented with nutrients (e.g., salts, amino acids, vitamins, trace elements, antioxidants) to promote the desired cellular activity, such as cell viability, growth, proliferation, and/or differentiation of the cells cultured in the media. A "base media," as used herein, refers to a basal salt nutrient or an aqueous solution of salts and other elements that provide cells with water and certain bulk inorganic ions essential for normal cell metabolism and maintains intra-cellular and/or extra-cellular osmotic balance. In some embodiments, a base media may include at least one carbohydrate as an energy source and/or a buffering system to maintain the medium within the physiological pH range. Examples of commercially available base media may include, but are not limited to, phosphate buffered saline (PBS), Dulbecco's Modified Eagle's Medium (DMEM), Minimal Essential Medium (MEM), Basal Medium Eagle (BME), Roswell Park Memorial Institute Medium (RPMI) 1640, MCDB 131, Click's medium, McCoy's 5A Medium, Medium 199, William's Medium E, insect media such as Grace's medium, Ham's Nutrient mixture F-10 (Ham's F-10), Ham's F-12, α-Minimal Essential Medium (αMEM), Glasgow's Minimal Essential Medium (G-MEM) and Iscove's Modified Dulbecco's Medium. See, e.g., US Patent Application Publication No. US20150175956.

"Hydrogel" as used herein refers to naturally-derived hydrogels and synthetic hydrogels. Naturally-derived hydrogels and synthetic hydrogels may be mixed to form hybrid hydrogels. Naturally-derived hydrogels may include, but not limited to, Matrigel®, which is made out of native extracellular matrix proteins collected from a cell line, collagen and alginate. Naturally-derived hydrogels may be derived from decellularized tissue extracts. Extracellular matrix may be collected from a specific tissue and may be used as or combined with a hydrogel material to be used to support cells of that tissue type. See, e.g., Skardal et al., *Tissue Specific Synthetic ECM Hydrogels for 3-D in vitro Maintenance of Hepatocyte Function*, Biomaterials 33 (18): 4565-75 (2012). Chitosan hydrogel is an example of a naturally-derived hydrogel that is degradable and supportive for several different cell types. See, e.g., Moura et al., *In Situ Forming Chitosan Hydrogels Prepared via Ionic/Covalent Co-Cross-Linking*, Biomacromolecules 12 (9): 3275-84 (2011). Hyaluronic acid hydrogels may also be used. See, e.g., Skardal et al., *A hydrogel bioink toolkit for mimicking native tissue biochemical and mechanical properties in bioprinted tissue constructs*, Acta Biomater. 25: 24-34 (2015).

Synthetic hydrogels may be produced from a variety of materials (e.g., Poly-(ethylene glycol)) and using many techniques. In contrast to naturally-derived hydrogels, synthetic hydrogels may be produced uniformly and may be easily reproducible and characterized. Synthetic hydrogels may, however, lack some functional signals for cells, like the active sites found in natural extracellular matrix, limiting their potential to support cells. See, e.g., Mahoney et al., *Three-Dimensional Growth and Function of Neural Tissue in Degradable Polyethylene Glycol Hydrogels*, Biomaterials 27 (10): 2265-74 (2006). Hybrid hydrogels may offer a compromise and may allow for more control over the ability to reconstruct a specific microenvironment. By combining natural components, such as extracellular matrix molecules (e.g., extracellular matrix proteins), with defined synthetic hydrogels, a more easily reproducible and functional hydrogels can be produced. See, e.g., Salinas et al., *Chondrogenic Differentiation Potential of Human Mesenchymal Stem Cells Photoencapsulated within Poly(Ethylene Glycol)—Arginine-Glycine-Aspartic Acid-Serine Thiol-Methacrylate Mixed-Mode Networks*, Tissue Engineering 13 (5): 1025-34 (2007).

The disclosures of all United States patent references cited herein are to be incorporated by reference to the extent that they are consistent with the disclosures herein.

1. Lung Organoids and Methods of Making the Same

Provided herein is an artificial mammalian lung organoid including (a) an epithelial cell layer including mammalian lung epithelial cells, (b) a stromal cell layer including mammalian lung fibroblast cells, and (c) an endothelial cell layer including mammalian endothelial cells. In some embodiments, the epithelial cell layer may include primary mammalian lung epithelial cells. In some embodiments, the stromal cell layer may include primary mammalian lung fibroblast cells or mammalian lung fibroblast cells differentiated from a stem cell or cell line, and the endothelial cell layer may include primary mammalian endothelial cells or mammalian endothelial cells differentiated from a stem cell or cell line. In some embodiments, the endothelial cell layer may also include microvascular endothelial cells. In some embodiments, the endothelial cell layer may include human umbilical vein endothelial cells (HUVEC).

In some embodiments, said mammalian lung epithelial cells, said mammalian lung fibroblast cells and/or said mammalian endothelial cells may be human cells. In some embodiments, the mammalian lung epithelial cells are polarized cells that include distinct "apical", "lateral" and "basal" plasma membrane domains. In some embodiments, polarized epithelial cells allow directional transport of molecules across the epithelial layer.

In some embodiments, the lung organoid may further include a membrane between said epithelial cell layer and said stromal lung cell layer and/or between said stromal lung cell layer and said endothelial lung cell layer.

FIGS. 1 (*a*), (*b*) and (*c*) provide schematic illustrations of the layers of lung organoids including membrane(s) according to some embodiments of the present invention. The lung organoid may include a membrane 10 between the epithelial cell layer 20 and the stromal lung cell layer 30 as illustrated in FIG. 1(*a*), may include a membrane 10 between the stromal lung cell layer 30 and the endothelial lung cell layer 40 as illustrated in FIG. 1(*b*) or may include a membranes 10 between the epithelial cell layer 20 and the stromal lung cell layer 30, and between the stromal lung cell layer 30 and the endothelial lung cell layer 40, respectively, as illustrated in FIG. 1(*c*). In some embodiments, the membrane(s) included in the lung organoid may be porous, allowing the flow or transport of molecules through them.

In some embodiments, lung organoids of the invention may be made by:

depositing an endothelial cell layer comprising live mammalian endothelial cells (e.g., microvascular endothelial cells) on a first side of a membrane (e.g., porous membrane);

depositing a stromal cell layer comprising live mammalian lung fibroblast cells on a second side of the membrane that is opposite the first side of the membrane; and depositing an epithelial cell layer comprising live mammalian lung epithelial cells directly on the stromal cell layer.

Cells may be obtained from established cultures, donors, biopsy, immortalized cell lines, stem cells, or a combination thereof. In some embodiments, cells are primary cells. In some embodiments, cells are human lung cells. In some embodiments, cells are passaged.

Depositing or seeding of the cells can be carried out by any suitable technique, including but not limited to spreading/painting, coating, spraying, etc. In some embodiments the depositing steps may be carried out by printing or bioprinting in accordance with any suitable technique, including "ink jet" type printing, syringe injection type printing or other methodology known in the art. Apparatus for carrying out such bioprinting is known and described in, for example, Boland et al., U.S. Pat. No. 7,051,654; Yoo et al., US Patent Application Pub. No. US 2009/0208466; and Kang et al., US Patent Application Publication No. US 2012/0089238.

As noted above, a membrane (e.g., a porous membrane) may be positioned at one or more junctions of the cell layers of the lung organoid. The membrane may be or include a polymeric material. The polymeric material may be synthetic, such as polystyrene, or derived from a natural tissue, such as a decelluarized extracellular matrix (ECM) or non-decelluarized extracellular matrix (ECM). In some embodiments, one or both sides of the membrane may be coated with ECM protein (e.g., laminin, collagen type I, collagen type IV, fibronectin and elastin), proteoglycan, vitronectin, poly-D-lysine and/or polysaccharide.

In some embodiments, one or both sides of the membrane may be coated on with a lung tissue-derived extracellular matrix composition or a hydrogel including a lung tissue-derived extracellular matrix composition. See, e.g., Lang et al., *Three-dimensional culture of hepatocytes on porcine liver tissue-derived extracellular matrix*, Biomaterials. 2011; 32(29):7042-7052; Mirmalek-Sani et al., *Porcine pancreas extracellular matrix as a platform for endocrine pancreas bioengineering*, Biomaterials. 2013; 34(22):5488-5495; Orlando et al., *Production and implantation of renal extracellular matrix scaffolds from porcine kidneys as a platform for renal bioengineering investigations*, Annals of surgery. 2012; 256(2):363-370; see also Booth et al., *Acellular normal and fibrotic human lung matrices as a culture system for in vitro investigation*, American Journal of Respiratory and Critical Care Medicine. 2012; 186(9):866-876. For example, the lung ECM biogel may be generated by solubilizing human lung ECM powder and combining the solubilized human lung ECM powder with a hydrogel. The human lung ECM powder may be made from decellularized or non-decellularized human lung ECM. The human lung ECM powder may be formed by lyophilizing human lung ECM and then grinding the lyophilized human lung ECM into a powder, e.g., with a freezer mill. See e.g., Y. Zhang et al., US Patent Application Publication No. 2013/0288375; and Skardal et al., *Tissue specific synthetic ECM hydrogels for 3-D in vitro maintenance of hepatocyte function*, Biomaterials 33(18): 4565-75 (2012).

In some embodiments, lung organoids of the invention may be made by:

providing a hydrogel including stromal cells (e.g., live mammalian lung fibroblast cells) therein;

depositing an endothelial cell layer comprising live mammalian endothelial cells (e.g., microvascular endothelial cells) on a first side of the hydrogel; and depositing an epithelial cell layer comprising live mammalian lung epithelial cells on a second side of the hydrogel that is opposite the first side of the hydrogel.

In some embodiments, the hydrogel may or may not be cross-linked. In some embodiments, the hydrogel may include gelatin, fibrinogen, gellan gum, pluronics (poloxamers), alginate, chitosan, hyaluronic acid, cellulose and/or collagen.

Figure 2:
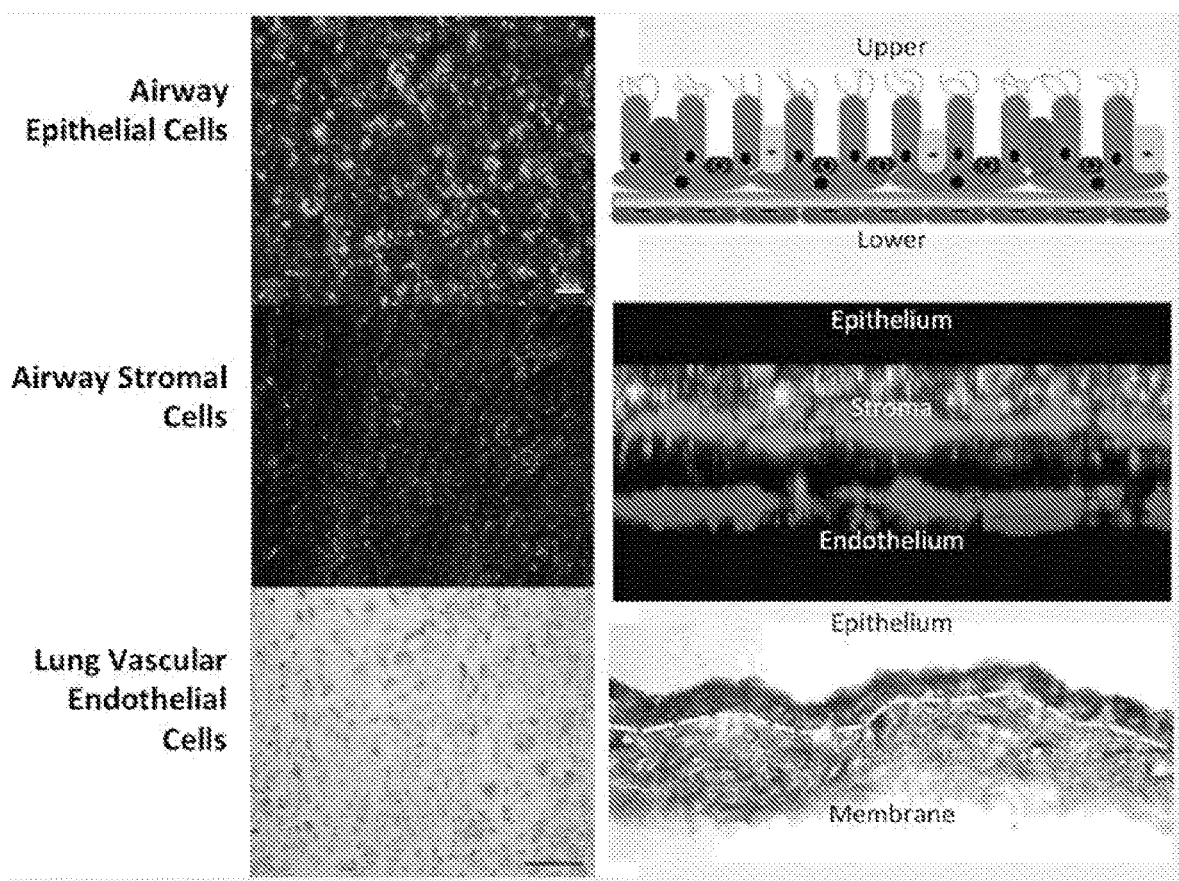
FIG. 2 shows a 3D lung organoid developed by layering fluorescent dye-labeled microvasculature endothelial cells and airway stromal mesenchymal cells with primary airway epithelium.

In some embodiments, 3D lung organoids may be formed by layering microvasculature endothelial cells (lower) and airway stromal mesenchymal cells (middle) with primary airway epithelium (upper) as illustrated in FIG. 2. The epithelial cells are polarized and ciliated. In some embodiments, endothelial cells may be labeled with fluorescent dye.

Figure 3:
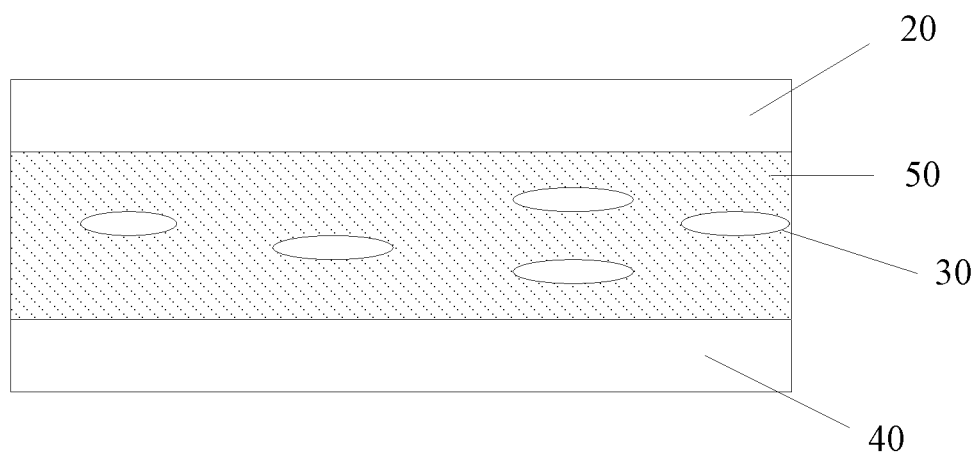
FIG. 3 provides a schematic illustration of a lung organoid including a hydrogel according to some embodiments of the present invention.

FIG. 3 provides a schematic illustration of a lung organoid including a hydrogel according to some embodiments of the present invention. Referring to FIG. 3, in some embodiments, the lung organoid may further include a hydrogel 50 that includes said stromal cells 30 therein. The epithelial cell layer 20 and endothelial cell layer 40 may be on opposing surfaces of the hydrogel 50, respectively. The hydrogel 50 may or may not be cross-linked. Examples of the hydrogel 50 include, but are not limited to, gelatin, fibrinogen, gellan gum, pluronics (poloxamers), alginate, chitosan, hyaluronic acid, cellulose, collagen, and mixtures thereof.

In some embodiments, the hydrogel 50 may include a lung tissue-derived extracellular matrix composition (a lung ECM biogel). In some embodiments, the stromal cells of the organoid may be suspended in the lung ECM biogel at physiological stiffness (1-2 kPa). In some embodiments, the hydrogel 50 may be a hyaluronic acid-based hydrogel. See e.g., Skardal et al., *A hydrogel bioink toolkit for mimicking native tissue biochemical and mechanical properties in bioprinted tissue constructs*, Acta Biomater. 25: 24-34 (2015); and PCT Application Publication No. WO 2016/064648A1, which is incorporated by reference herein.

In some embodiments, the lung organoid may be infected by a viral or bacterial lung pathogen. Pathogens that cause respiratory disease include the common flu or influenza (A or B; Orthomyxoviridae family), respiratory syncytial virus, human parainfluenza viruses (HPIVs; paramyxovirus family), metapneumovirus (hMPV; family Paramyxoviridae), adenoviruses, rhinoviruses, parainfluenza viruses, coronaviruses, coxsackievirus, and herpes simplex virus. Respiratory disease bacterial pathogens include *Yersinia pestis, Bacillus anthracis, Escherichia coli, Pseudomonas aeruginosa, Francisella tularensis, Staphylococcus aureus* Group A beta-hemolytic streptococci (GABHS), group C beta-hemolytic streptococci, *Corynebacterium diphtheriae, Neisseria gonorrhoeae, Arcanobacterium haemolyticum, Chlamydia pneumoniae, Mycoplasma pneumoniae, Streptococcus pneumoniae, Haemophilus influenzae, Moraxella catarrhalis, Bordetella pertussis*, and *Bordetella parapertussis*.

2. Devices and Systems

In some embodiments, the lung organoid may be provided in a microfluidic device. Various microfluidic device configurations useful for the support of organoids are known in the art. See, e.g., US Patent Application Publication No. 2014/0038279 to Ingber et al.; Bhatia and Ingber, "Microfluidic organs-on-chips," Nature Biotechnology 32:760-772 (2014).

In general, a microfluidic device including the lung organoid as taught herein may include a chamber so dimensioned to accept the lung organoid therein such that the lung organoid defines a boundary between a first chamber or opening in fluid contact with the epithelial cell layer of the lung organoid, and a second chamber or opening in fluid contact with the endothelial cell layer of the lung organoid. The fluid may be a liquid such as media, or a gas such as air. The device may further include a fluid inlet and fluid outlet for each chamber, fluid reservoirs connected therewith, etc. In some embodiments, a gas (e.g., air) may contact the epithelial cell layer of the lung organoid, and a liquid (e.g., media) may contact the endothelial cell layer of the lung organoid. In some embodiments, a microfluidic device may be provided in the form of a cartridge for "plug in" or insertion into a larger apparatus including pumps, culture media reservoir(s), detectors, and the like.

Figure 4:
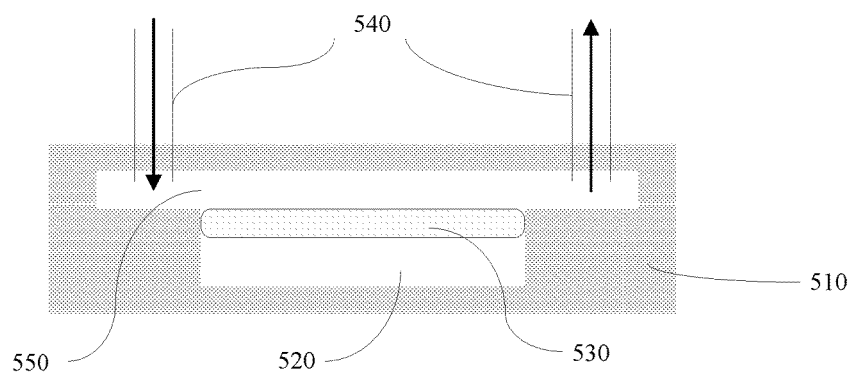
FIG. 4 (a) is a schematic diagram of a microfluidic device according to some embodiments of the present invention.
Figure 4:
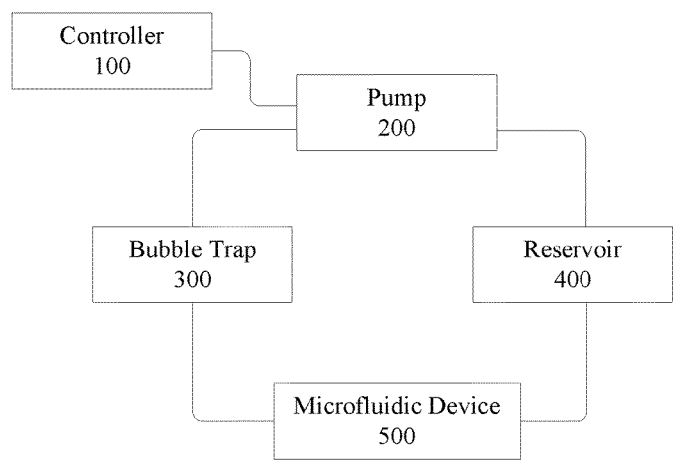
Figure 4:
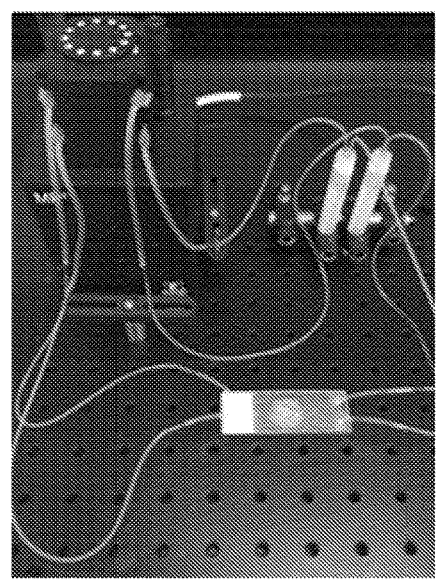

FIG. 4 (a) is a schematic diagram of a microfluidic device according to some embodiments of the present invention. Referring to FIG. 4(a), in some embodiments, a microfluidic device may include a housing 510 and a chamber 520 in the housing 510. A lung organoid 530 may be placed in the chamber 520. The microfluidic device may further include a fluid inlet and fluid outlet 540 through which fluid (e.g., media, air) may come in and out and a channel or an opening 550 which are provided for fluid connection of the lung organoid 530 to the fluid. In some embodiments, at least a portion of the microfluidic device housing 510 may be transparent to allow imaging the lung organoid 530. In some embodiments, the microfluidic device may include multiple fluid inlets and outlets 540 and multiple channels 550 for providing different types of fluids to the lung organoid 530. In some embodiments, electrodes of a trans-endothelial (or epithelial) electrical resistance (TEER) sensor may be provided in the housing 510 of the microfluidic device (not shown).

FIG. 4 (b) is a schematic diagram of a microfluidic support system according to some embodiments of the present invention. Referring to FIG. 4(b), the microfluidic support system may include one or more of a controller 100 for pump control (e.g., a computer), a pump 200 (e.g., a peristaltic pump), a bubble trap 300, a media reservoir 400 and a microfluidic device 500. It will be understood that the microfluidic support system may include multiple reservoirs 400 for different types of media or other fluids.

FIG. 4 (c) is an image of a microfluidic support system according to some embodiments of the present invention. The microfluidic support system includes two media reservoirs that have a cylindrical shape and are connected to a pump through tubing and a microfluidic device that has a rectangular shape and is connected to both the media reservoirs and the pump through the tubing to form a closed-loop system.

3. Methods of Use

The lung organoids as described herein may be used as an alternative to live animal testing for compound or vaccine screening (e.g., screening for efficacy, toxicity, or other metabolic or physiological activity) or for treatment of (including resistance to treatment of) lung infection or disease (e.g., chronic obstructive pulmonary disease (COPD)). For acute treatment testing, compound or vaccine may be applied, e.g., once for several hours. For chronic treatment testing, compound or vaccine may be applied, e.g., for days to one week. Such testing may be carried out by providing a lung organoid product as described herein under conditions which maintain constituent cells of that product alive (e.g., in a culture media with oxygenation); applying a compound to be tested (e.g., a drug candidate) to the lung organoid (e.g., by topical or vapor application to the epithelial layer); and then detecting a physiological response (e.g., damage, scar tissue formation, infection, cell proliferation, burn, cell death, marker release such as histamine release, cytokine release, changes in gene expression, etc.), the presence of such a physiological response indicating said compound or vaccine has therapeutic efficacy, toxicity, or other metabolic or physiological activity if inhaled or otherwise delivered into the lung of a mammalian subject. A control sample of the lung organoid may be maintained under like conditions, to which a control compound (e.g., physiological saline, compound vehicle or carrier) may be applied, so that a comparative result is achieved, or damage can be determined based on comparison to historic data, or comparison to data obtained by application of dilute levels of the test compound, etc.

It will be understood that the lung organoids as described herein can be an excellent tool to study drug delivery since the lung organoids include both an epithelial cell layer and an endothelial cell layer. The endothelial cell layer of the lung organoids may be exposed to a liquid (e.g., media) and may function as a mature vascular barrier that controls materials passing through the endothelial cell layer. The epithelial cell layer of the lung organoids may be exposed to a gas (e.g., air) and thus may be exposed to materials delivered by aerosol. In some embodiment, the epithelial cell layer may include cilia.

Methods of determining whether a test compound has immunological activity may include testing for immunoglobulin generation, chemokine generation and cytokine generation by the cells.

4. Storing and Shipping of Devices

Once produced, the devices described above may be used immediately, or prepared for storage and/or transport.

To store and transport the device, a transient protective support media that is a flowable liquid at room temperature (e.g., 25° C.), but gels or solidifies at refrigerated temperatures (e.g., 4° C.), such as a gelatin mixed with water, may be added into the device to substantially or completely fill the chamber(s), and preferably also any associated conduits. Any inlet and outlet ports may be capped with a suitable capping element (e.g., a plug) or capping material (e.g., wax). The device may be then packaged together with a cooling element (e.g., ice, dry ice, a thermoelectric chiller, etc.) and all may be placed in a (preferably insulated) package.

In some embodiments, to store and transport the device, a transient protective support media that is a flowable liquid at cooled temperature (e.g., 4° C.), but gels or solidifies at warm temperatures such as room temperature (e.g., 20° C.) or body temperature (e.g., 37° C.), such as poly(N-isopropylacrylamide) and poly(ethylene glycol) block co-polymers, may be added into the device to substantially or completely fill the chamber(s), and preferably also any associated conduits.

Upon receipt, the end user may simply remove the device from the associated package and cooling element, may allow the temperature to rise or fall (depending on the choice of transient protective support media), may uncap any ports, and may remove the transient protective support media with a syringe (e.g., by flushing with growth media).

The present invention is explained in greater detail in the following non-limiting Examples.

EXAMPLES

An airway organoid was constructed using primary normal human bronchial epithelial (NHBE) cells, primary human lung fibroblasts and human endothelial cells (HUVEC), as found in the normal human upper airway, layered on a polyester membrane in an order and ratio to replicate human airway tissue.

1. Construction of Lung Organoid

Each side of a polyester membrane (Corning® Costar® Snapwell™ cell culture inserts, 12 mm with 0.4 μm pore, pore density 4×106 pores/cm$^2$, polyester membrane, TC-treated, sterile) was coated with 150 μl collagen IV (Sigma C7521) and left under the biosafety hood overnight (hood open and blower on). The membrane was UV sterilized for 30 mins the next morning.

250,000 HUVECs (endothelial cells) (Cell and Viral Vector Core Laboratory, Wake Forest University) were seeded on the underside of the membrane and let stand for up to 4 hours for cells to attach. Membrane was then placed with 2 ml of EGM-10 in the well of the 6 well plate.

250,000 HALF (human adult lung fibroblasts, isolated from donor) were seeded on the upper side of the membrane and covered with 200 µl of DMEM-F12 1:1 (Hyclone SH30261.01).

After 5-7 days, a layer of 250,000 cells NHBE cells (epithelial cells) (Lonza Cat #CC2540) was established over the layer of fibroblasts and covered with 200 µl BEGM (Clonetics CC4175).

Change media: EGM 10 and BEGM—Once every 2 days; DMEM—Once every 3-4 days by carefully pipetting off 100 µl media from the top of the transwell (for HALF& NHBE) without touching the cells and replacing it with the same amount of fresh media.

Primary cell types were characterized by PCR and flow cytometry to demonstrate normal cell phenotype using Vybrant® Multicolor Cell-Labeling Kit V-22889 (Used for labeling cells for imaging). p63-α (D2K8X) XP® Rabbit mAb #13109, Anti-Dynein intermediate chain 1 antibody [74.1] (ab23905) and Anti-Mucin 5AC antibody [45M1] (ab3649) were used for characterization of NHBE by flow-cytometry.

A microfluidic device was used to provide physiological flow of media to both sides of the membrane, or alternatively, to the lower side only, producing an air-liquid interface established at the upper membrane.

Pathogenesis of *Bordetella pertussis* was studied in this model by analyzing trans-epithelial resistance, the levels of toxins and cytokines, imaging by fluorescent microscopy.

2. Results and Discussion

Characterization of cells: Primary lung fibroblasts maintained expression of fibroblast-specific markers during passaging, while NHBE cells maintained expression of markers for basal, goblet, ciliated and clara cells during culture.

Normal human lung fibroblasts are tested for expression of von Willebrand factor/Factor VIII, cytokeratins 18 and 19, and alpha smooth muscle actin. Lung microvascular endothelial cells express CD31/105, von Willebrand Factor, and PECAM. Human Primary lung Epithelial cells express markers basal (p63+ KRT5+), ciliated (Foxj1+ Sox17+), Clara (Scgb1A1+) mucosal (Muc5ac+) cell numbers and CFTR+ epithelial cells.

Organoid Development: Fluorescent labeling of the cells of the airway organoid demonstrated that the cells formed distinct cell layers representative of endothelial vasculature, the stromal component and a polarized epithelial monolayer. TEM and histological imaging confirmed the development of a multi-layered upper airway organoid construct.

Maintenance of cells in microfluidic system: The airway organoid maintained in the microfluidic system remained viable and facilitated non-invasive analysis of *Bordetella pertussis* pathogenesis.

CONCLUSION

Multiple primary airway cell types were combined to generate a functional upper airway organoid. This bioengineered organoid system is useful in conducting studies into human disease, toxicity studies and drug and vaccine development.

The foregoing is illustrative of the present invention, and is not to be construed as limiting thereof. The invention is defined by the following claims, with equivalents of the claims to be included therein.

That which is claimed is:

1. An artificial mammalian lung organoid, comprising:
(a) an epithelial cell layer comprising mammalian lung epithelial cells;
(b) a stromal cell layer comprising mammalian lung fibroblast cells; and
(c) an endothelial cell layer comprising mammalian endothelial cells,
wherein said organoid further comprises a porous membrane between said epithelial cell layer and said stromal cell layer and/or between said stromal cell layer and said endothelial cell layer, and
wherein at least one side of said porous membrane is coated with a lung tissue-derived extracellular matrix composition.

2. The lung organoid of claim 1, wherein the mammalian lung epithelial cells are polarized.

3. The lung organoid of claim 1, wherein the mammalian endothelial cells are human cells.

4. The lung organoid of claim 1, wherein the mammalian lung fibroblast cells are human cells.

5. The lung organoid of claim 1, wherein the mammalian lung epithelial cells are human cells.

6. The lung organoid of claim 1, wherein said organoid is an upper airway lung organoid.

7. The lung organoid of claim 1, wherein the mammalian lung epithelial cells are bronchial epithelial cells.

8. The lung organoid of claim 1, wherein the mammalian lung epithelial cells comprise normal bronchial epithelial cells.

9. The lung organoid of claim 8, wherein the bronchial epithelial cells comprise basal, goblet, ciliated and/or clara cells.

10. The lung organoid of claim 1, wherein the mammalian lung epithelial cells comprise diseased bronchial epithelial cells.

11. The lung organoid of claim 1, wherein a ratio of the mammalian lung fibroblast cells of the stromal cell layer and the mammalian endothelial cells of the endothelial cell layer is from 2:1 to 1:2.

12. The lung organoid of claim 1, wherein a ratio of the mammalian lung fibroblast cells of the stromal cell layer and the mammalian lung epithelial cells of the epithelial cell layer is from 2:1 to 1:2.

13. The lung organoid of claim 1, wherein said porous membrane comprises a polymeric material.

14. The lung organoid of claim 1, wherein said extracellular matrix composition is collagen.

15. The lung organoid of claim 1, wherein said lung tissue-derived extracellular matrix composition is derived from a decellualized lung extracellular matrix.

16. The lung organoid of claim 1, further comprising a hydrogel, wherein said stromal cell layer is in said hydrogel.

17. The lung organoid of claim 16, wherein said hydrogel comprises gelatin, fibrinogen, gellan gum, poloxamers, alginate, chitosan, hyaluronic acid, cellulose and/or collagen.

18. The lung organoid of claim 16, wherein said hydrogel comprises an extracellular matrix composition.

19. The lung organoid of claim 18, wherein said extracellular matrix composition comprises a lung extracellular matrix composition.

20. The lung organoid of claim 1, wherein said organoid is infected with a lung pathogen.

21. The lung organoid of claim 1, wherein said organoid is infected with *Bordetella pertussis* or *Pseudomonas aeruginosa*.

22. The lung organoid of claim 1, wherein the lung organoid comprises a single porous membrane between said stromal cell layer and said endothelial cell layer, and said epithelial cell layer directly contacts said stromal cell layer.

23. A microfluidic device comprising the lung organoid of claim 1, the device comprising a housing comprising a chamber and a channel,
  wherein the lung organoid is in the chamber,
  wherein the channel is configured to provide fluid connection of the lung organoid to a fluid inlet and a fluid outlet, and
  wherein said fluid inlet and said fluid outlet are connected to a fluid reservoir.

24. The microfluidic device of claim 23, wherein at least a portion of the housing is transparent.

25. The microfluidic device of claim 23, wherein the endothelial cell layer of the lung organoid is in fluid connection with a liquid.

26. The microfluidic device of claim 23, wherein the epithelial cell layer of the lung organoid is in fluid connection with a gas.

27. The microfluidic device of claim 23, wherein the epithelial cell layer of the lung organoid is in fluid connection with a liquid.

28. An artificial mammalian lung organoid, comprising:
  an epithelial cell layer comprising mammalian lung epithelial cells;
  an endothelial cell layer comprising mammalian endothelial cells; and
  a hydrogel comprising mammalian lung fibroblast cells, wherein the hydrogel is between the epithelial cell layer and the endothelial cell layer and directly contacts both the epithelial cell layer and the endothelial cell layer.

29. The lung organoid of claim 28, wherein said hydrogel comprises an extracellular matrix composition comprising a lung tissue-derived extracellular matrix composition.

30. An artificial mammalian lung organoid, comprising:
  (a) an epithelial cell layer comprising mammalian lung epithelial cells;
  (b) a stromal cell layer comprising mammalian lung fibroblast cells; and
  (c) an endothelial cell layer comprising mammalian endothelial cells,
  optionally wherein said organoid further comprises a porous membrane between said epithelial cell layer and said stromal cell layer and/or between said stromal cell layer and said endothelial cell layer, and
  wherein a ratio of the mammalian lung fibroblast cells of the stromal cell layer and the mammalian endothelial cells of the endothelial cell layer is from 2:1 to 1:2.

31. An artificial mammalian lung organoid, comprising:
  (a) an epithelial cell layer comprising mammalian lung epithelial cells;
  (b) a stromal cell layer comprising mammalian lung fibroblast cells; and
  (c) an endothelial cell layer comprising mammalian endothelial cells,
  optionally wherein said organoid further comprises a porous membrane between said epithelial cell layer and said stromal cell layer and/or between said stromal cell layer and said endothelial cell layer, and
  wherein a ratio of the mammalian lung fibroblast cells of the stromal cell layer and the mammalian lung epithelial cells of the epithelial cell layer is from 2:1 to 1:2.

\* \* \* \* \*